(12) United States Patent
Goto (10) Patent No.: US 7,019,745 B2
(45) Date of Patent: Mar. 28, 2006

(54) THREE-DIMENSIONAL IMAGE DISPLAY DEVICE

(75) Inventor: Yoshihiro Goto, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 342 days.

(21) Appl. No.: 10/471,548

(22) PCT Filed: Oct. 3, 2001

(86) PCT No.: PCT/JP01/08716

§ 371 (c)(1),
(2), (4) Date: Sep. 11, 2003

(87) PCT Pub. No.: WO02/078545

PCT Pub. Date: Oct. 10, 2002

(65) Prior Publication Data

US 2004/0075658 A1    Apr. 22, 2004

(30) Foreign Application Priority Data

Mar. 28, 2001   (JP)   .............................. 2001-92944

(51) Int. Cl.
*G06T 15/50*   (2006.01)
(52) U.S. Cl. .................. 345/426; 382/128; 382/131
(58) Field of Classification Search ............. 345/426; 382/131

See application file for complete search history.

(56) References Cited

U.S. PATENT DOCUMENTS

| | | | | |
|---|---|---|---|---|
| 5,782,762 A | * | 7/1998 | Vining | 600/407 |
| 5,871,266 A | * | 2/1999 | Negishi et al. | 353/98 |
| 5,883,933 A | * | 3/1999 | Goto et al. | 378/62 |

* cited by examiner

*Primary Examiner*—Richard Hjerpe
*Assistant Examiner*—Andrew Yang
(74) *Attorney, Agent, or Firm*—Antonelli, Terry, Stout and Kraus, LLP.

(57) ABSTRACT

A three-dimensional image display apparatus emphasizes display of a particular portion using the volume rendering method, where a volume image constructed by aligning a plurality of tomograms is shaded and projected on a predetermined projection plane to produce a 3D image. A volume rendering method is used where, in an algorithm for shading, virtual light beams are radiated from a virtual light source set outside the volume image, and pixel values on the projection plane are calculated based on reflectivity and density gradient of light beams at the respective pixels on the projection plane. At a luminescence ratio allocating area, a luminescence ratio is allocated for amplifying light beams entering pixels representing a particular object to be emphasized. The thus-allocated luminescence ratio is added as a parameter of the shading calculation in the volume rendering method and is used for calculation of pixel values on the projection plane.

3 Claims, 6 Drawing Sheets

THREE-DIMENSIONAL IMAGE DISPLAY DEVICE

TECHNICAL FIELD

The present invention relates to a three-dimensional image display apparatus; and, more particularly, the invention relates to a three-dimensional image display apparatus for constructing and displaying a three-dimensional image, using the volume rendering method to shade a plurality of tomograms obtained by a medical imaging apparatus, such as an X-ray CT apparatus or an MRI apparatus.

BACKGROUND OF THE INVENTION

In accordance with conventional techniques, it is well known that, by using an X-ray CT apparatus, an MRI apparatus, or an ultrasonic apparatus, a tomogram of an object to be examined can be obtained. Also, the volume rendering method, the surface rendering method, the depth method and the like are known methods of constructing a three-dimensional image (3D image) by shading, on a projection plane, a volume image that has been constructed by aligning a plurality of such tomograms.

Incidentally, the volume rendering method is mentioned in the document "Marc Levoy; "Display of Surfaces from Volume Data", IEEE Computer Graphics & Applications, pp29–37, 1988."

However, it is substantially impossible to emphasize the display of a particular portion of a 3D image that is constructed by the conventional volume rendering method so as to easily distinguish it from other portions. For example, it has been impossible to emphasize display of a particular lesion area so as to easily find it in a diagnostic examination, or to emphasize display of a stent graft in order to explain to a patient how it has been inserted in a blood vessel during surgery. Even if the particular lesion area or the stent graft is provided with colors, they are not displayed distinctively from other portions.

The object of the present invention is to provide a three-dimensional image display apparatus that can construct and display a three-dimensional image where a particular portion is emphasized in a display by using the volume rendering method.

SUMMARY OF THE INVENTION

To achieve the above-stated object, a three-dimensional image display apparatus according to the present invention projects a volume image that is constructed by aligning a plurality of tomograms on a predetermined projection plane using the volume rendering method, and displays a three-dimensional image using the volume rendering method where light beams are radiated from a virtual light source that is set outside the volume image in an algorithm for shading, and pixel values of the projection plane are calculated based on the reflectivity and the density gradient of the light beams at the respective pixels of the volume image. The three-dimensional image display apparatus includes luminescence ratio allocating means for allocating a greater luminescence ratio to the light beams applied to the pixels corresponding to a particular object to be emphasized in the display over other objects in the volume image, and calculating means for adding the luminescence ratio allocated by the luminescence ratio allocating means as a parameter of the shading calculation in the volume rendering method and for calculating pixel values on the projection plane, wherein the particular object to which the greater luminescence ratio is allocated is emphasized in display.

Further, the luminescence ratio allocating means has light emission patterns matching lesions in each portion of the body to be examined, in which specific luminescence ratios are allocated to density values of pixels representing the lesions, and the luminescence ratio corresponding to a lesion of the portion is selected by selecting the lesion of the portion to be emphasized in the display.

That is, when a particular lesion area is chosen to be emphasized in the display, only a light emission pattern corresponding to the lesion is selected, and, if there is a lesion, the lesion area is displayed luminously (becomes bright).

Further, a three-dimensional image display apparatus projects a volume image constructed by aligning a plurality of tomograms with shading on a predetermined projection plane and thus displays a three-dimensional image, using the volume rendering method, where, in an algorithm for shading, light beams are radiated from a virtual light source set outside the volume image and pixel values on the projection plane are calculated based on the reflectivity and the density gradient of the light beam at the pixels of the projection plane. The three-dimensional image display apparatus includes color luminescence ratio allocating means for allocating a color luminescence ratio to pixels showing a particular object to be emphasized in the display among all the objects to be displayed, and calculating means for adding the color luminescence ratio allocated by the color luminescence ratio allocating means as a parameter for shading calculation in the volume rendering method and thus calculating the pixel values on the projection plane, whereby the particular object to which the color luminescence ratio is allocated is emphasized in the display.

That is, when a particular lesion area is chosen to be emphasized in the display, only the color luminescence ratio corresponding to the lesion is selected, and, if there is such a lesion, that lesion area is displayed with a color.

DETAILED DESCRIPTION OF THE PREFERRED EMBODIMENT

Various embodiments of the three-dimensional image display apparatus according to the invention will be described with reference to the drawings.

Figure 1:
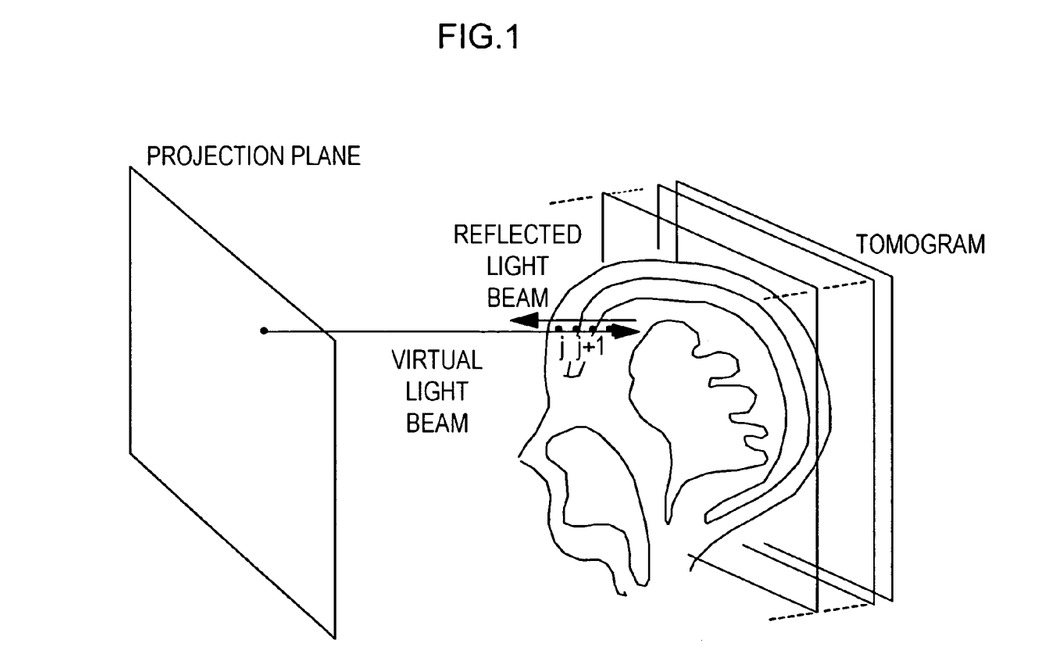
FIG. 1 is a diagram illustrating shading by the volume rendering method.

First, a system of constructing a 3D image by the volume rendering method according to the invention will be described. Generally, in the volume rendering method, each pixel of a volume image constructed by aligning a plurality of tomograms, as shown in FIG. 1, is referred to as a voxel having a cubic shape. Therefore, a volume image is an image constructed by three-dimensionally aligning the voxels. The data of a voxel is the measured CT value calculated on the basis of the X-ray absorption at the portion of a human body corresponding to that voxel when an X-ray CT apparatus is used, and it is based on the measured proton density when an MRI apparatus is used.

Parameters for shading, in the volume rendering method, include the opacity of light set according to the CT values and the gradient of contour lines of the CT values (hereinafter referred to as a density gradient).

In the surface rendering method, a suitable threshold CT value condition is set, and those pixels meeting this condition are extracted. On the other hand, in the volume rendering method, pixels with CT values which indicate a suitably determined degree of opacity are extracted. By use of either rendering method a desired object, such as bone and skin, can be exclusively extracted, and the pixel values of the object can be used as a parameter for shading on the projection plane.

That is, the virtual light beams radiated by the virtual light source, as shown in FIG. 1, which pass through the respective voxels of the volume image, are attenuated according to the opacity determined by the CT values at the respective voxels. Consequentially, the size of reflected lights at the respective voxels can be measured. In the shading algorithm according to the volume rendering method, a voxel becomes brighter as the size of a reflected light becomes larger. Further, it is assumed that a virtual surface exists where the CT value of a voxel greatly changes, and the voxel is made brighter as the virtual surface faces more to the front, that is, as the concentration gradient is larger.

The sum of brightness values of voxels along the line from the viewpoint toward the depth direction until the virtual light beam is attenuated to 0 is regarded as the value representing the brightness of the respective pixels on the projection plane (hereinafter referred to as pixel value), and the pixel values of all pixels on the projection plane are calculated.

According to this invention, a pixel value on the projection plane is calculated in accordance with the formula 1 so as to emphatically display the particular portion:

Pixel value on the projection plane $$\text{Pixel value on the projection plane} = \text{fixed value} \times \sum_{j=0}^{k} \xi(Vj) \cdot \Delta^{\delta(Vj)} \cdot \left\{ 1 - \sum_{j=0}^{j-1} [\xi(Vj) + \eta(Vj)] \right\} \quad \text{(formula 1)}$$

where V: CT value, density value;
ξ: reflectivity;
η: luminescence ratio (negative absorption ratio);
Δ: concentration gradient; and
δ(V): actual number substantially in the range from 0.1 to 6.0, a function of V.

Intensity of incident light beam is assumed to be 1.

As shown by the formula 1, the pixel value on the projection plane is the information acquired by summing the brightness value of each voxel (j=0 to k) along the path of a virtual light beam. Here, k is the number of voxels that the virtual light beam passes through while being reflected and attenuated at each voxel until the beam intensity becomes 0 (that is, the value within { } of the formula 1 becomes 0).

According to the invention, the luminescence ratio η(Vj) having a negative value is added to two parameters within [ ] in the formula 1. That is, although the virtual light beam is generally attenuated at each pass through a voxel and is not amplified, according to the invention, a luminescence ratio proportional to the intensity of the incident light beam is allocated to the voxels of the portion chosen to be emphasized in the display, and, consequentially, the intensity of the incident light beams is amplified at the voxels of the portion chosen to be emphasized in the display.

Figure 2:
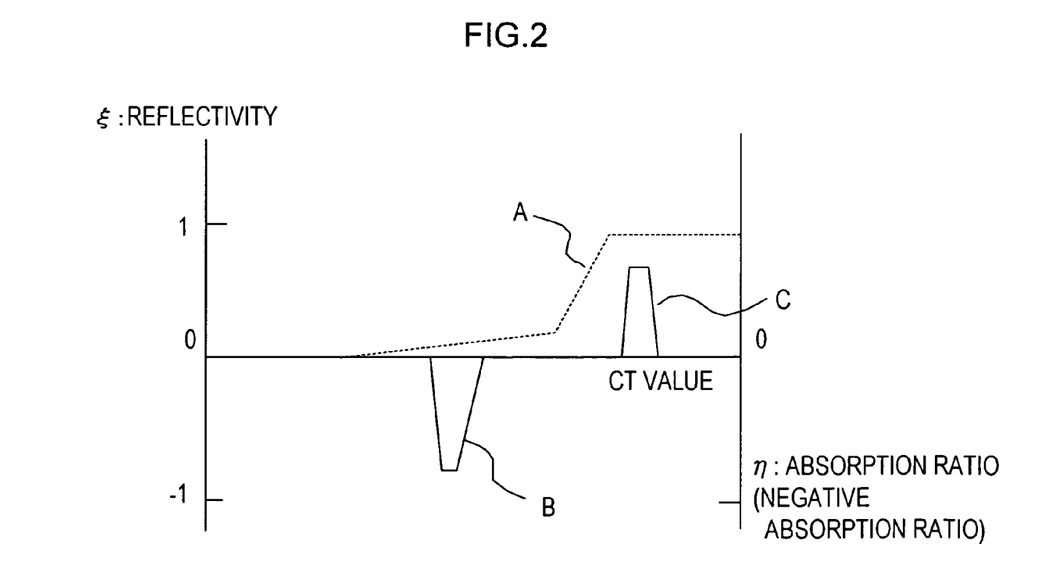
FIG. 2 is a graph of the luminescence ratio according to the invention.

FIG. 2 shows one example of the reflectivity pattern A, where the reflectivity ξ is allocated according to the CT value of the voxels, and the reflectivity pattern B, where the luminescence ratio η is allocated thereto. Incidentally, the luminescence ratio η has a negative value and increases the value of { } in the formula 1 (that is, the intensity of the incident light beam). Further, in FIG. 2, C represents a pattern of the absorption ratio, and the luminescence ratios as defined above can be made similar to the negative absorption ratio of the virtual light beam.

Figure 3:
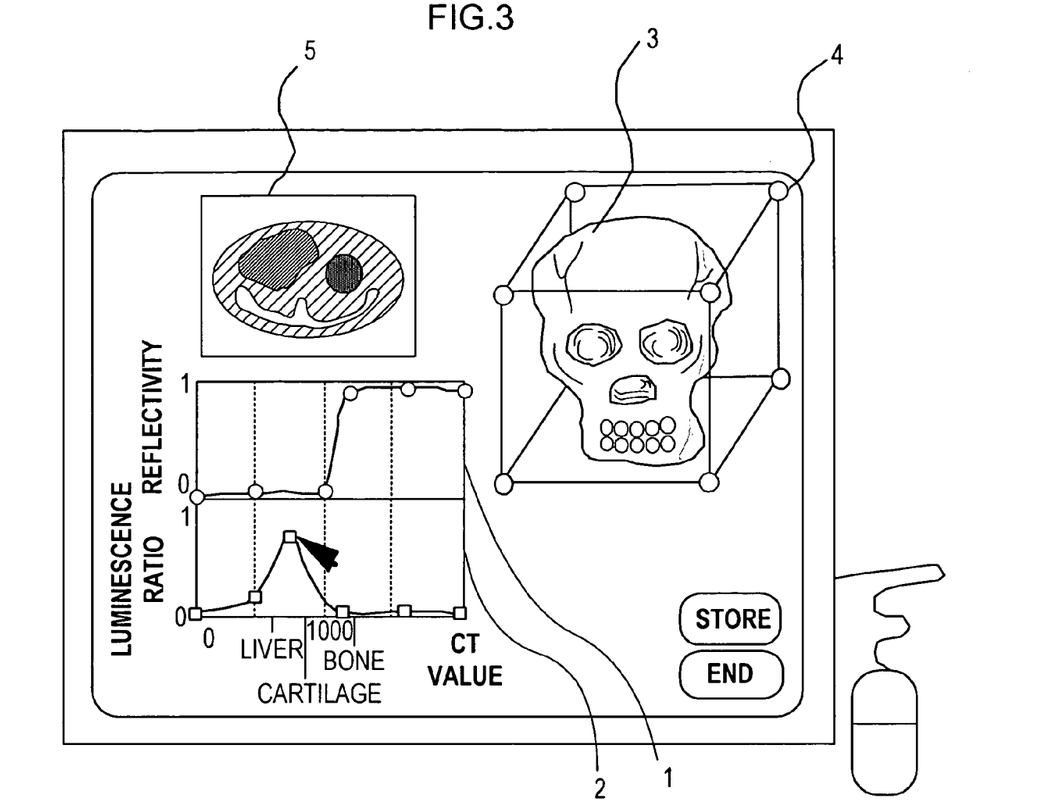
FIG. 3 is a diagram showing one example of a display monitor of a CRT display illustrating the display of a 3D image constructed according to the invention.

FIG. 3 shows an example of the display monitor of a CRT display for displaying a 3D image and the like that has been constructed on the basis of formula 1.

As shown in the figure, at a reflectivity allocating area 1, ○ marks are moved with a mouse to allocate a desired reflectivity to CT values. Similarly, at a luminescence ratio allocating area 2, □ marks are moved with the mouse to allocate a desired luminescence ratio to CT values. The pixel values on the projection plane are calculated from the formula 1, based on the thus-allocated reflectivity and luminescence ratio, and a 3D image 3 is constructed and displayed.

Also, at the luminescence ratio allocating area 2, a lesion area of the liver, cartilage, bone, and the like can be selected by the mouse. When a desired lesion area is selected from among such lesion areas, a luminescence ratio pattern for emphasizing the display of the lesion area is also set automatically.

Incidentally, to shift the point of view of the 3D image 3 within a cube, the white circles 4 on the corners of the cube are dragged by the mouse and the cube is rotated suitably with respect to the center point of the cube. Consequentially, the direction of the sight line of the 3D image 3 is determined, and a 3D image is newly constructed and displayed. The thus-constructed 3D image is stored in a magnetic disk when needed. Further, in FIG. 3, the reference number 5 represents a tomogram (CT image).

Figure 4:
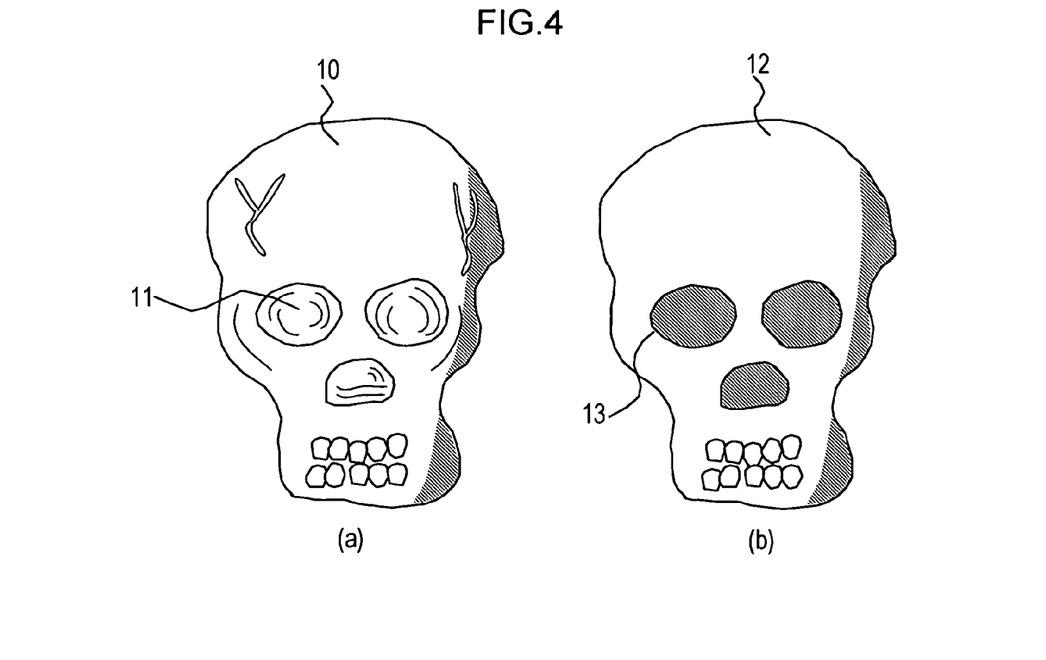
FIGS. 4(a) and 4(b) are diagrams showing one example of a 3D image displayed according to the invention and a conventional 3D image, respectively.

FIG. 4(a) shows a 3D image 10 of a head constructed by setting a luminescence ratio to CT values corresponding to the brain, and FIG. 4(b) shows a 3D image 12 of head constructed without setting a luminescence ratio (luminescence ratios of all CT values are 0). The brain (particularly the eyeball portion 11), as shown in FIG. 4(a) is brightly displayed, and the brain (particularly the eyeball portion 13), as shown in FIG. 4(b), is darkly displayed.

Figure 5:
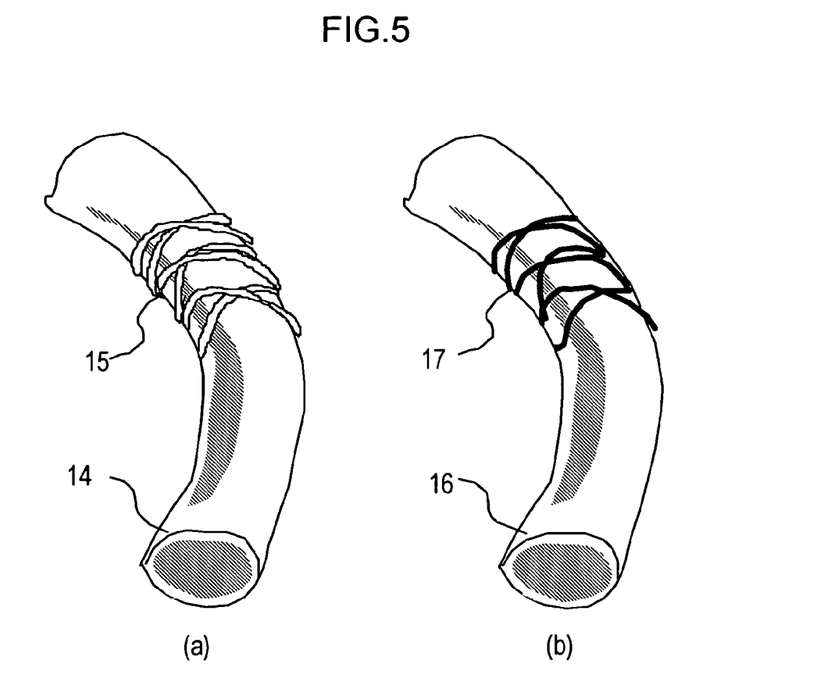
FIGS. 5(a) and 5(b) are diagrams showing another example of a 3D image displayed according to the invention and a conventional 3D image, respectively.

Further, FIG. 5(a) shows a 3D image 14 of a blood vessel constructed by setting a luminescence ratio to CT values corresponding to a stent graft 15, and FIG. 4(b) shows a 3D image 16 of a blood vessel constructed without setting a luminescence ratio. The stent graft 15 shown in FIG. 5(a) is brightly displayed, and the stent graft 17 shown in FIG. 5(b) is darkly displayed.

Figure 6:
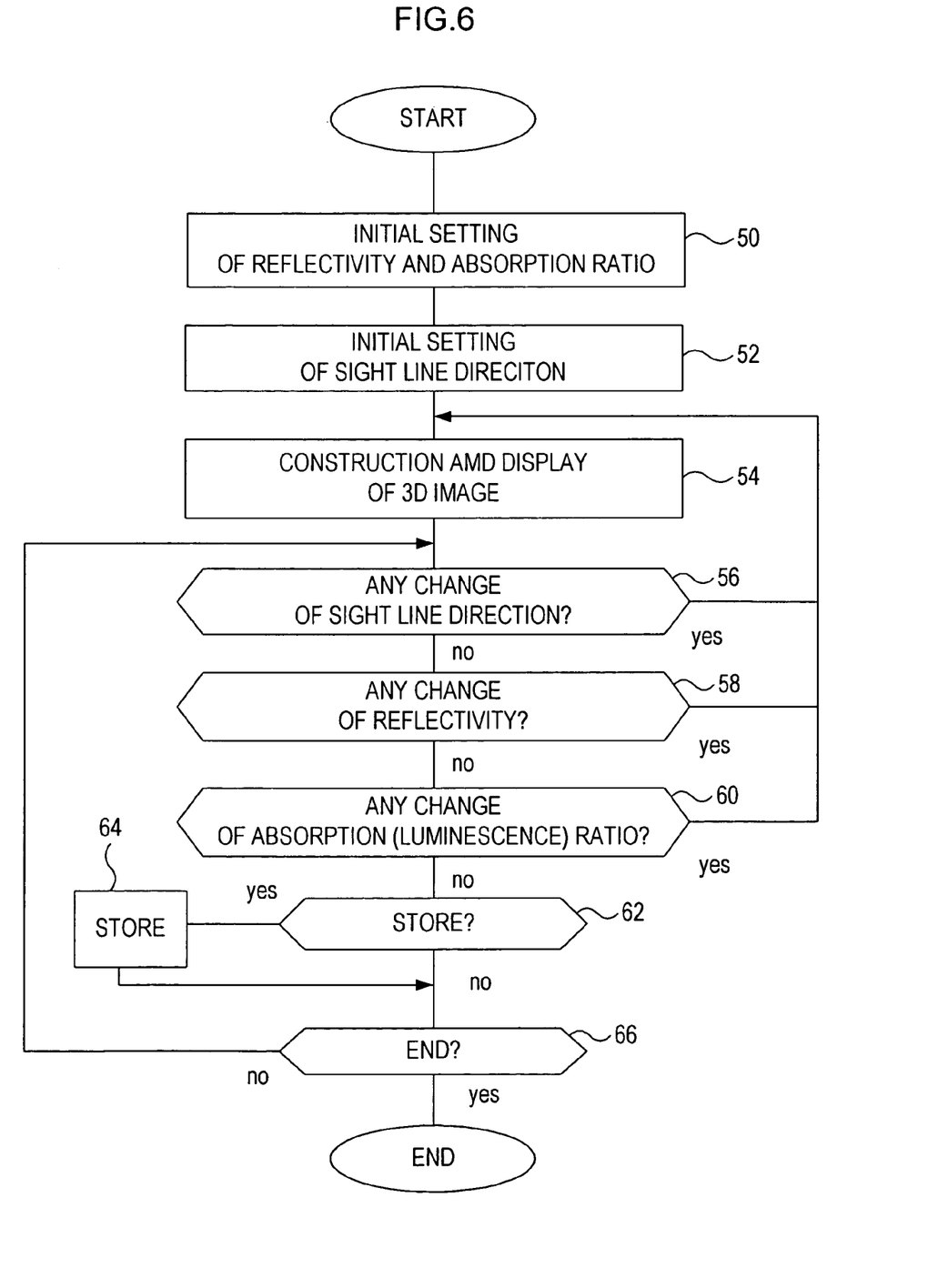
FIG. 6 is a flow chart showing the procedure of 3D image display according to the invention.

FIG. 6 is a flow chart showing the procedure employed in displaying a 3D image according to the invention.

[Step 50]

Reflectivity, luminescence ratios, and initial values are set.

[Step 52]

Initial values in the direction of the sight line (the direction of the virtual light beam) are set.

[Step 54]

Pixel values on the projection plane are calculated based on the formula 1, and a 3D image is constructed and displayed. To display the 3D image on the CRT display, values in the projection plane memory are converted with reference to a table for adjusting values to fit the display tone and then they are written in a display memory, and the 3D image is thus displayed.

[Step 56, 58, 60]

It is judged whether the sight line direction, the reflectivity, or the luminescence ratio is changed or not. If any of them is changed, the procedure jumps to the step 54 and the 3D image is again constructed and displayed.

[Step 62]

It is judged whether the 3D image displayed at this point is stored or not. If there is an instruction to store it, the procedure jumps to step 64. If not, the procedure goes to step 66.

[Step 64]

The 3D image displayed at this point is stored in a magnetic disk.

[Step 66]

It is judged whether there is an instruction to end the 3D image display or the like. If there is no instruction to end processing, the procedure jumps to step 56. If there is an instruction to end, the processing operation is ended.

Figure 7:
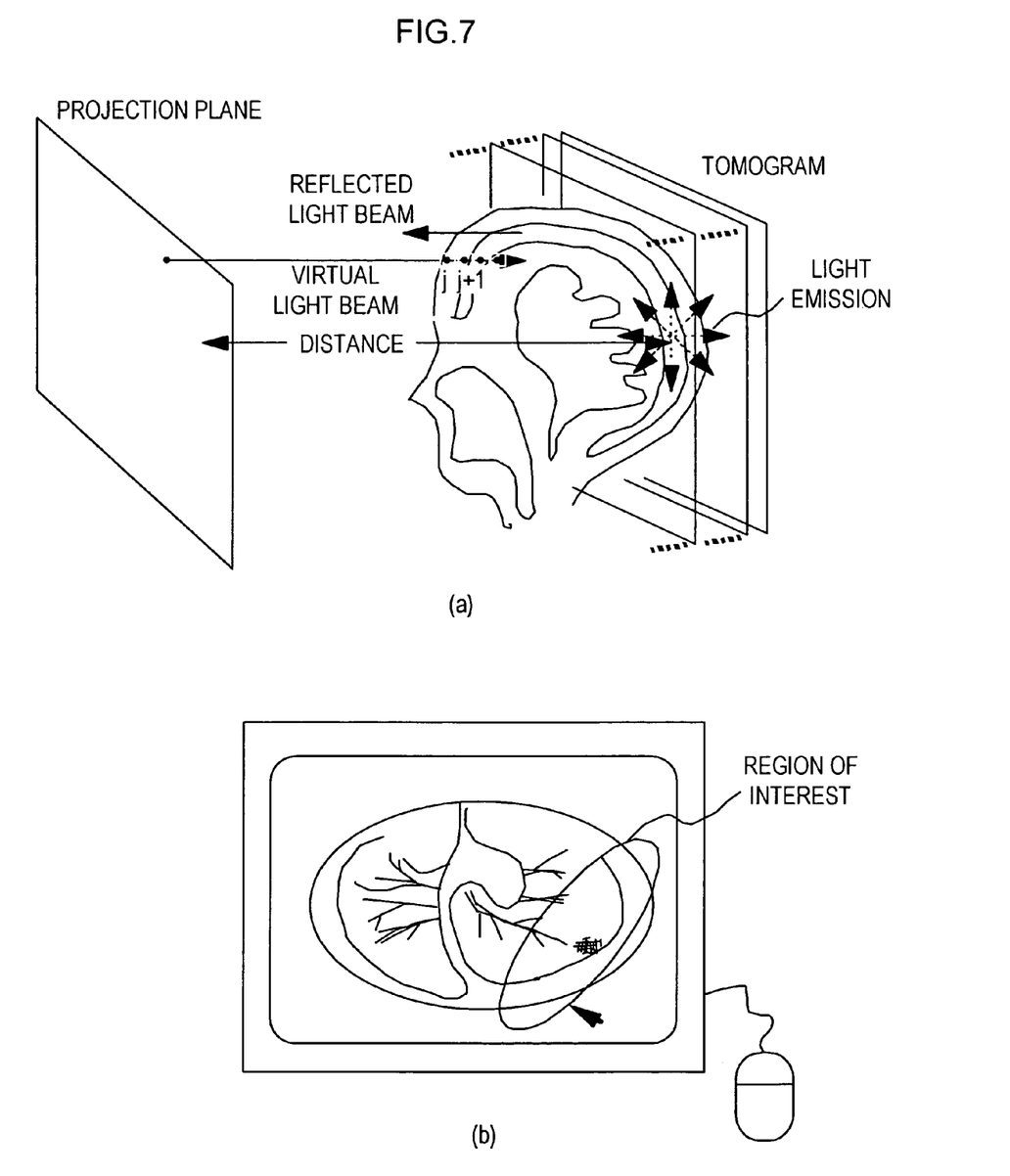
FIGS. 7(a) and 7(b) are diagrams illustrating an example of the setting of luminescence ratios and colors according to the invention.

Further, as shown in FIG. 7, the portion which is made to emit light may be a particular region of interest. This region of interest is determined by the distance between the projection plane and the portion emitting light, as shown in FIG. 7(a). The region of interest is set when the operator encloses the desired region in the displayed image using a mouse, as shown in FIG. 7(b), and the setting in the depth direction is made when the operator suitably sets the distance between the desired light-emitting portion and the projection plane.

Further, although the above description is directed mainly to monochrome display, it goes without saying that the invention can be applied to color display as well. In this case, the color display can be realized by converting the luminescence ratio in the monochrome image into a color luminescence ratio in the color image.

Figure 8:
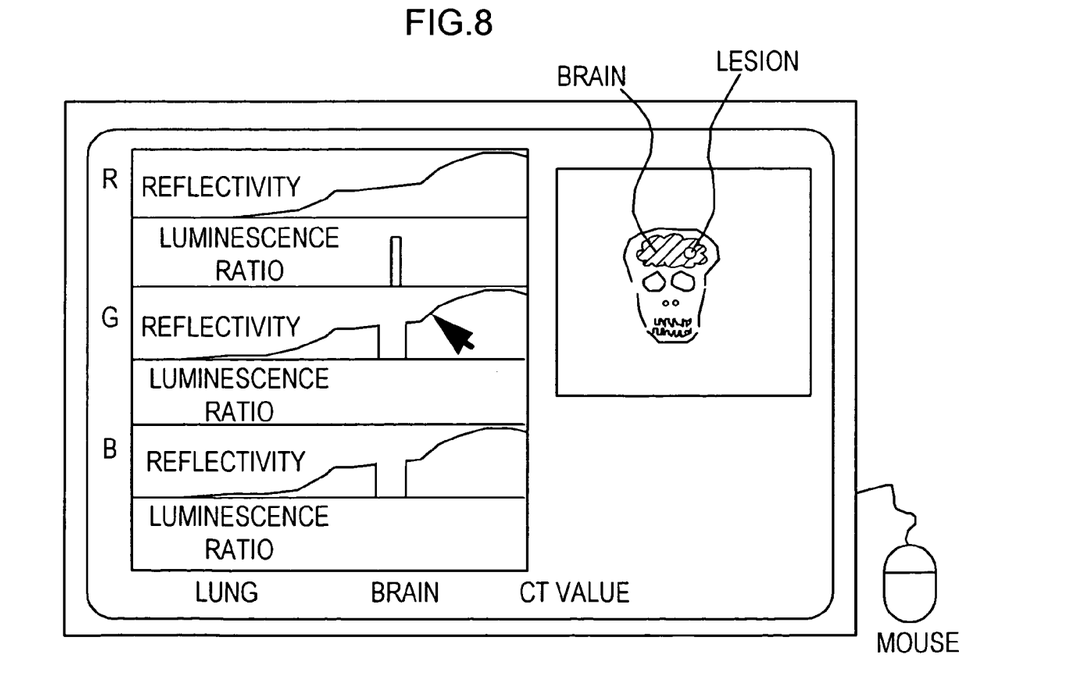
FIG. 8 is a diagram showing an example of the setting of colors to be generated and an example of the display thereof according to the invention.

More specifically, as shown in FIG. 8, color components of red (R), green (G), and blue (B) can be separately emitted. The horizontal axis represents CT values. For example, when the brain is chosen to emit red light, the light reflectivity (opacity) of the components G and B in the range of CT values showing the brain is controlled to be low by mouse operation, and thus the luminescence ratio of the component R becomes larger. Consequentially, the brain emits red light. Incidentally, this colored light emission is just an example, and it goes without saying that colors that do not depend on a coloring system determined by RGB are also included.

Figure 9:
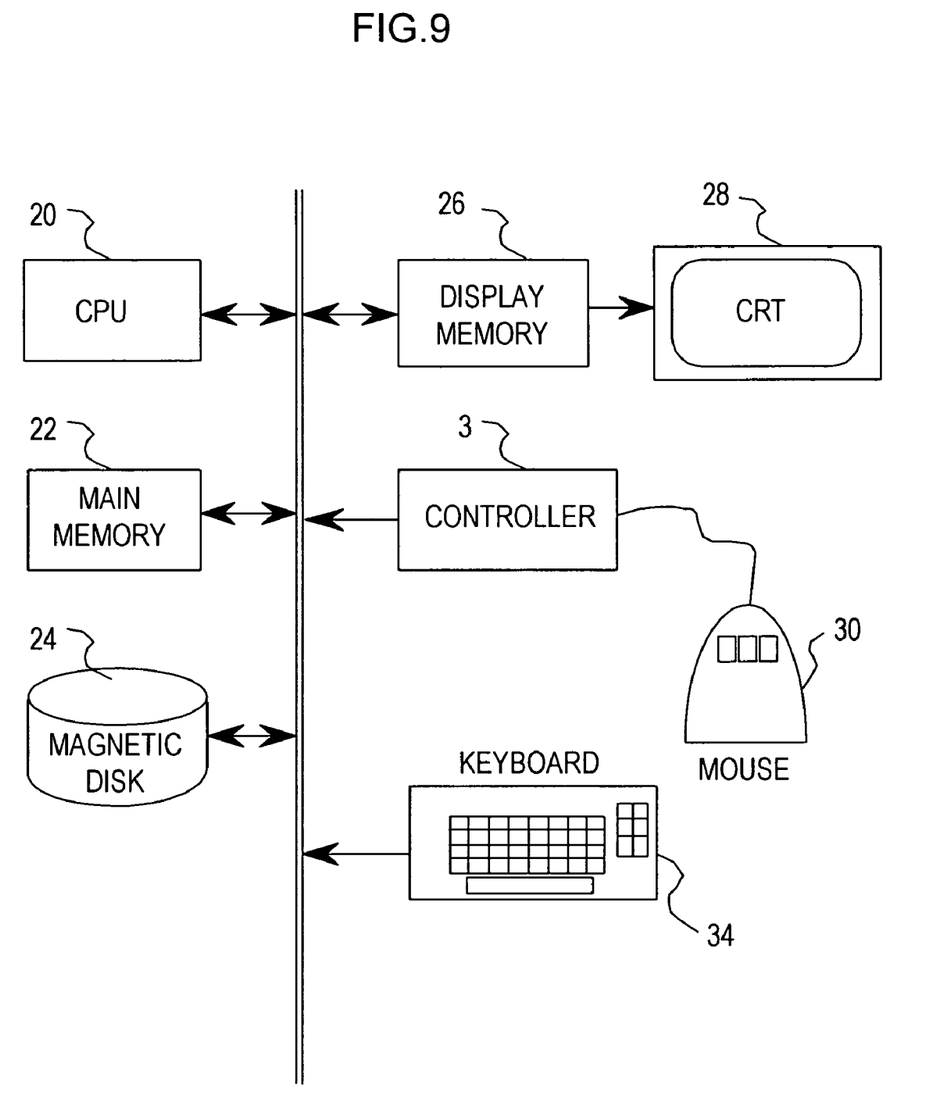
FIG. 9 is a block diagram showing the hardware configuration of a three-dimensional image display apparatus according to the invention.

FIG. 9 is a block diagram showing an example of the hardware configuration of the three-dimensional image display apparatus according to the invention. This three-dimensional image display apparatus constructs and displays a 3D image based on the above-mentioned formula 1 from a plurality of tomograms of a portion of the object obtained by an X-ray CT apparatus. For example, the apparatus includes a central processing unit (CPU) 20 for controlling operation of each component; a main memory 22 where control programs of the apparatus are stored; a magnetic disk 24 where data of a plurality of tomograms and programs are stored; a display memory 26 for temporarily storing image data for display; a CRT monitor 28 serving as a display device for displaying an image based on the image data received from the display memory 26; a mouse 30 serving as a position inputting device; a mouse controller 32 for detecting the state of the mouse 30 and for outputting to the CPU 20 signals indicating the position of the mouse pointer on the CRT monitor 18 and the state of the mouse 30; a keyboard 34 for inputting instructions to conduct various operations; and a common bus 26 for connecting each of the above components.

Incidentally, in this embodiment, the pixel values on the projection plane are calculated, based on the above-mentioned formula 1, to construct a 3D image; however, the invention is not limited thereto, and the pixel values on the projection plane also may be calculated by the following formula 2 and formula 3:

$$\text{Pixel value on the projection plane} = \text{fixed value} \times \sum_{j=0}^{k} [\xi(Vj) + C \cdot \eta(Vj)] \cdot \Delta^{\delta(Vj)} \cdot \left\{ 1 - \sum_{j=0}^{j-1} [\xi(Vj) + \eta(Vj)] \right\} \quad \text{(formula 2)}$$

where C is a constant;

$$\text{Pixel value on the projection plane} = \text{fixed value} \times \sum_{j=0}^{k} \xi(Vj) \cdot \Delta^{\delta(Vj)} \cdot \sum_{j=0}^{j-1} \{1 - [\xi(Vj) + \eta(Vj)]\} \quad \text{(formula 3)}$$

These formulas are added to increase the reflectivity and for image enhancement. Further, according to the formula 3, the incident intensity is multiplied and then attenuated. Since the attenuation of the incident intensity is slower than that in the formula 1, a 3D image of portion that is located further inside the body can be constructed.

Further, according to the above-described invention, the luminescence ratio and the color to be emitted are respectively allocated; however, it is also included in the invention that they are combined and a particular portion or stent graft is emphasized in the display as a result of such combinations.

As described above, according to the invention a three-dimensional image can be displayed where a particular portion is emphasized in the display by use of the volume rendering method, whereby the invention has the effect that a lesion area can be easily found in a health examination, and the like.

What is claimed is:

1. A three-dimensional image display apparatus for displaying a three-dimensional image by shading a volume image constructed by aligning a plurality of tomograms and projecting it on a projection plane using a volume rendering method where, in an algorithm for shading, light beams are radiated from a virtual light source set outside the volume image and pixel values on the projection plane are calculated based on the reflectivity and the density gradient of the light beams at the respective pixels of the volume image, the three-dimensional image display apparatus including luminescence ratio allocating means for allocating a luminescence ratio for amplifying light beams entering the pixels representing a particular object to be emphasized in the display and calculating means for calculating pixel values on the projection plane by adding the above-allocated luminescence ratio as a parameter of a shading calculation in the volume rendering method, wherein the particular object to which the luminescence is allocated is emphasized in the display.

2. A three-dimensional image display apparatus according to claim 1, wherein said luminescence ratio allocating means has luminescence ratio patterns for lesions in the respective portions of the object, each pattern allocating a luminescence ratio to pixels with density values indicating a lesion in that portion, and by choosing the portion whose lesion is to be emphasized in the display, the luminescence pattern corresponding to that portion is selected.

3. A three-dimensional image display apparatus for displaying a three-dimensional image by shading a volume image constructed by aligning a plurality of tomograms and projecting it on a predetermined projection plane using a volume rendering method where, in an algorithm for shading, virtual light beams are radiated from a virtual light source set outside the volume image and pixel values on the projection plane are calculated based on the reflectivity and the density gradient of the light beams at the respective pixels of the volume image, the three-dimensional image display apparatus including color luminescence ratio allocating means for allocating a color luminescence ratio to pixels representing a particular object to be emphasized in the display among objects to be displayed in the volume image and calculating means for adding, as a parameter of a shading calculation in the volume rendering method, the color luminescence ratio allocated to the pixels by luminescence ratio allocating means and calculating pixel values on the projection plane, whereby the particular object to which the color luminescence ratio is allocated is emphasized in the display.

* * * * *